United States Patent
Heo et al.

(10) Patent No.: US 9,381,498 B2
(45) Date of Patent: Jul. 5, 2016

(54) METHOD FOR PREPARING HYDROGENATION CATALYST AND METHOD FOR PREPARING DIOLS FROM LACTONES USING THE HYDROGENATION CATALYST

(71) Applicant: Samsung Electronics Co., Ltd., Suwon-si, Gyeonggi-do (KR)

(72) Inventors: Hyeonsu Heo, Uijeongbu-si (KR); Jongmin Lee, Hwaseong-si (KR); Kyunghae Lee, Incheon (KR); Jun Chwae, Seoul (KR); Mooho Lee, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/680,405

(22) Filed: Apr. 7, 2015

(65) Prior Publication Data

US 2016/0030928 A1    Feb. 4, 2016

(30) Foreign Application Priority Data

Jul. 31, 2014    (KR) .................. 10-2014-0098629

(51) Int. Cl.
| | |
|---|---|
| *B01J 21/08* | (2006.01) |
| *C07C 31/20* | (2006.01) |
| *B01J 23/78* | (2006.01) |
| *C07C 29/143* | (2006.01) |
| *B01J 37/04* | (2006.01) |
| *B01J 37/06* | (2006.01) |
| *B01J 37/02* | (2006.01) |

(52) U.S. Cl.
CPC .............. *B01J 23/78* (2013.01); *B01J 37/0201* (2013.01); *B01J 37/04* (2013.01); *B01J 37/06* (2013.01); *C07C 29/143* (2013.01)

(58) Field of Classification Search
CPC ........ B01J 21/08; B01J 23/78; B01J 37/0201; B01J 37/04; B01J 37/06; B01J 37/08; B01J 37/14; C07C 29/143; C07C 31/20; C07C 31/207

USPC .................. 502/243, 244, 330, 331; 568/862; 516/81, 97, 98
See application file for complete search history.

(56) References Cited

U.S. PATENT DOCUMENTS

| | | | | |
|---|---|---|---|---|
| 4,497,908 | A * | 2/1985 | Lewis ................. | B01J 23/8946 502/245 |
| 4,585,890 | A | 4/1986 | Miyazaki et al. | |
| 4,652,685 | A | 3/1987 | Cawse et al. | |
| 4,764,498 | A * | 8/1988 | Wissner ................ | B01J 21/08 502/232 |
| 4,780,448 | A * | 10/1988 | Broecker ................ | B01J 23/72 502/174 |
| 4,797,382 | A * | 1/1989 | De Thomas ......... | B01J 23/8926 502/241 |
| 4,855,273 | A | 8/1989 | Pohl et al. | |
| 4,885,411 | A | 12/1989 | De Thomas et al. | |
| 5,099,038 | A | 3/1992 | Suzuki et al. | |
| 5,110,954 | A * | 5/1992 | Bellis .................. | C07D 315/00 549/266 |
| 5,302,568 | A | 4/1994 | Matsuda et al. | |
| 7,427,579 | B2 * | 9/2008 | Lee ........................ | B01J 23/002 502/232 |
| 2003/0069456 | A1 * | 4/2003 | Lee .......................... | B01J 23/72 568/861 |
| 2011/0301022 | A1 * | 12/2011 | Murakami ............ | B01J 23/002 502/242 |

FOREIGN PATENT DOCUMENTS

| | | | | |
|---|---|---|---|---|
| JP | 08-188544 | * | 7/1996 | ............. C07C 31/20 |
| KR | 10-2002-0042397 | * | 6/2002 | ............. C07C 29/151 |
| KR | 20020042397 A | | 6/2002 | |

* cited by examiner

*Primary Examiner* — Patricia L Hailey
(74) *Attorney, Agent, or Firm* — Leydig, Voit & Mayer, Ltd.

(57) ABSTRACT

A method for preparing a hydrogenation catalyst by mixing a copper salt with colloidal silica to form a precipitate, washing the formed precipitate to remove anions of the copper salt from the precipitate, and impregnating the anion-removed precipitate with an alkali metal to form a hydrogenation catalyst; and a method for preparing a diol from a lactone using the hydrogenation catalyst.

14 Claims, No Drawings

METHOD FOR PREPARING HYDROGENATION CATALYST AND METHOD FOR PREPARING DIOLS FROM LACTONES USING THE HYDROGENATION CATALYST

CROSS-REFERENCE TO RELATED APPLICATIONS

This application claims the benefit of Korean Patent Application No. 10-2014-0098629, filed on Jul. 31, 2014, in the Korean Intellectual Property Office, the entire disclosure of which is hereby incorporated by reference.

BACKGROUND OF THE INVENTION

1. Field

The present disclosure relates to methods for preparing hydrogenation catalysts and methods for preparing diols from lactones using the hydrogenation catalysts.

2. Description of the Related Art

Diols are compounds including two hydroxyl groups. Diols may be chemically prepared from lactones through hydrogenation reactions using hydrogenation catalysts. However, existing processes for preparing diols using hydrogenation catalysts have limitations in terms of process and facility costs since high reaction temperatures and large amounts of the catalysts are required in said processes.

Thus, there is a need in the art for efficient methods of preparing hydrogenation catalysts for preparing diols from lactones, and methods of preparing diols using the catalysts.

SUMMARY OF THE INVENTION

Provided is a method for preparing a hydrogenation catalyst including copper, colloidal silica and alkali metal. The method comprises mixing a copper salt with colloidal silica to form a precipitate; washing the precipitate to remove an anion of the copper salt from the precipitate; and impregnating the precipitate with an alkali metal to form a hydrogenation catalyst.

Also provided is a method for preparing a diol from a lactone by reacting a lactone with hydrogen in the presence of a hydrogenation catalyst to form a diol, wherein the hydrogenation catalyst is prepared as described herein.

DETAILED DESCRIPTION OF THE INVENTION

Additional aspects will be set forth in part in the description which follows and, in part, will be apparent from the description, or may be learned by practice of the presented exemplary embodiments.

Provided is a method for preparing a hydrogenation catalyst including mixing a copper salt with colloidal silica to form a precipitate, washing the formed precipitate to remove anions of the copper salt from the precipitate to form an anion-removed precipitate, and impregnating the anion-removed precipitate with an alkali metal to form a hydrogenation catalyst.

Any copper salt may be used. Examples of the copper salt may include $Cu(NO_3)_2$, $CuCl_2$, $Cu(CH_3COO)_2$, $CuSO_4$, or combinations thereof. The copper salt may be prepared in a form of an aqueous solution, and then, the solution may be mixed with colloidal silica.

The term "colloidal silica" refers to a suspension (e.g., colloidal suspension of amorphous silica (i.e., $SiO_2$) particles in a liquid phase. Colloidal silica particles are typically spherical and/or non-porous. The colloidal silica may be dispersed (suspended) in an aqueous solvent or organic solvent as the liquid phase. The colloidal silica may be directly prepared or may be obtained from commercially available colloidal silica products.

The copper salt and colloidal silica may be mixed in at a mixing ratio of about 15:2 to about 5:2, about 5:1 to about 3:1, or about 30:7 to about 10:3 based on the weights of Cu and $SiO_2$ in the copper salt and colloidal silica, respectively. In other words, the copper salt and colloidal silica are mixed in amounts that provide a weight ratio of Cu to $SiO_2$ of about 15:2 to about 5:2, about 5:1 to about 3:1, or about 30:7 to about 10:3. For example, the copper salt and colloidal silica may be mixed at a mixing ratio of about 15:4 based on the weights of Cu and $SiO_2$ in the copper salt and colloidal silica, respectively.

The method may include, after mixing the copper salt with colloidal silica, adding an alkaline precipitant to the mixture to adjust the pH of the mixture and form a precipitate. Examples of the alkaline precipitant include sodium hydroxide, potassium hydroxide, or ammonium hydroxide. The precipitate may be formed at a pH value in the range of about 8.5 to about 11, about 8.7 to about 10.5, about 8.9 to about 10.3, about 9.0 to about 10.0, about 9.0 to about 9.8, about 9.0 to about 9.5, or about 9.1 to about 9.3.

The method may include washing the formed precipitate to remove anions of the copper salt from the precipitate. For example, when the precipitate is formed by mixing copper nitrate with colloidal silica, the method may include washing the precipitate with distilled water several times to remove nitrate ions. The washing can be repeated, as necessary, to remove most or substantially all of the nitrate ions from the precipitate. Thereafter, the method may additionally include drying the precipitate to remove water from the precipitate. The drying step may be conducted at a temperature of about 100° C. to about 120° C. for any suitable amount of time to remove water from the precipitate.

The method may include impregnating the washed (e.g., anion-removed) precipitate with an alkali metal. The alkali metal may be lithium, sodium, potassium, rubidium, cesium, or combinations thereof. The weight of the alkali metal may be in a range of about 1/20 to about 1/2, about 1/20 to about 7/20, about 1/20 to about 1/4, about 3/20 to about 7/20, or about 3/20 to about 3/10 with respect to the weight of $SiO_2$ of the colloidal silica to be mixed with the copper salt. The impregnation step may be performed using a solution including an alkali metal salt. For instance, the precipitate can be contacted with the alkali metal salt solution in a manner that allows the alkali metal salt to penetrate the precipitate, such as by soaking or immersing the precipitate in the alkali metal salt solution or otherwise effecting sufficient contact with the precipitate (e.g., spraying or saturating) to permit the alkali to impregnate the precipitate.

The method may additionally include drying and calcination steps after the impregnation step. The drying step may be conducted at a temperature of about 100° C. to about 120° C. The calcination step may be conducted at a temperature of about 300° C. to about 550° C.

According to another embodiment, provided is a method for preparing a diol from a lactone. The method includes reacting a lactone with hydrogen in the presence of a hydrogenation catalyst prepared as described above to form a diol.

The term "lactone" refers to a compound including an ester group in a ring (i.e., a cyclic organic ester). The lactone may be γ-butyrolactone (GBL), β-propiolactone, δ-valerolactone, ε-caprolactone, α-angelica lactone, β-angelica lactone, γ-valerolactone (GVL), or combinations thereof. For example, when the lactone is γ-butyrolactone, a diol prepared by the reaction of the lactone with hydrogen in the presence of the hydrogenation catalyst may be 1,4-butanediol.

The reaction may be performed in a reaction temperature range of about 130° C. to about 250° C., about 140° C. to about 250° C., about 140° C. to about 200° C., about 145° C. to about 180° C., about 145° C. to about 175° C., or about 150° C. to about 170° C. The reaction may be performed under a pressure range of about 30 atm to about 70 atm, about 35 atm to about 65 atm, about 37 atm to about 62 atm, or about 40 atm to about 60 atm. The reaction may be performed in a weight hourly space velocity (WHSV) range of about 0.2/hr to about 1.2/hr, about 0.3/hr to about 1.2/hr, about 0.3/hr to about 1.5/hr, about 0.4/hr to about 1.2/hr, or about 0.5/hr to about 1.0/hr. The reaction may be performed with a molar ratio of hydrogen to lactone in a range of about 30 to about 100, about 50 about 100, about 60 to about 120, about 65 to about 110, about 70 to about 105, or about 75 to about 100.

EXAMPLES

Reference will now be made in detail to exemplary embodiments. In this regard, the present exemplary embodiments may have different forms and should not be construed as being limited to the descriptions set forth herein.

Comparative Example 1

Preparation of Copper Catalysts Using Fumed Silica or Colloidal Silica 1.1 Preparation of a Copper Catalyst Using Fumed Silica 5 g of fumed silica (Sigma-Aldrich) was impregnated with 10 ml of a solution prepared by dissolving 76.04 g of copper (II) nitrate trihydrate [(Cu(NO$_3$)$_2$.3H$_2$O] into 10 ml of distilled water. After the impregnated catalyst was dried and milled at about 110° C. for about 24 hours, the dried and milled catalyst was calcined at about 550° C. for about 3 hours to prepare an 80% Cu/SiO$_2$-F catalyst.

1.2 Preparation of a Copper Catalyst Using Colloidal Silica

1N NaOH (Sigma-Aldrich) was added to 10 ml of a solution prepared by dissolving 76.04 g of copper(II) nitrate trihydrate [(Cu(NO$_3$)$_2$.3H$_2$O] into 10 ml of distilled water to obtain a mixed solution with an adjusted pH value of about 9.2, and 16.7 g of colloidal silica (30 wt. % suspension in H$_2$O, Sigma-Aldrich) was slowly added to the pH adjusted mixed solution to result in coprecipitation. A precipitated slurry was washed with water five times to remove other salts except Cu and SiO$_2$. After the salt-removed slurry was dried at about 110° C. for about 24 hours, the dried slurry was calcined at about 550° C. for about 3 hours to prepare a 80% Cu/SiO$_2$—C catalyst.

Example 1

Preparation of a Copper Catalyst Using Colloidal Silica and an Alkali Metal

1N NaOH (Sigma-Aldrich) was added to 10 ml of a solution prepared by dissolving 71.3 g of copper(II) nitrate trihydrate [(Cu(NO$_3$)$_2$.3H$_2$O] into 10 ml of distilled water to obtain a mixed solution with an adjusted pH value of about 9.2, and 16.7 g of the same colloidal silica that was used in 1.2 Preparation of a copper catalyst using colloidal silica of the Comparative Example 1 was slowly added to the pH adjusted mixed solution to result in coprecipitation. A precipitated slurry was washed with water five times to remove other salts except Cu and SiO$_2$. Thereafter, the salt-removed slurry was dried at about 110° C. for about 24 hours to remove water from the slurry. The water-removed precipitate was additionally impregnated with 1.8 g of potassium hydroxide. After the potassium hydroxide-impregnated precipitate was dried at about 110° C. for about 24 hours, the dried precipitate was calcined at about 550° C. for about 3 hours to prepare a 75% Cu/SiO$_2$—C+5% K catalyst.

Example 2

Comparisons of Hydrogenation Reactions of Catalysts 2.1 Hydrogenation Reaction of γ-Butyrolactone After reducing the Cu/SiO$_2$—F catalyst, the Cu/SiO$_2$—C catalyst, and the Cu/SiO$_2$—C+5% K catalyst that had been prepared according to the above-described methods, a hydrogenation reaction for converting γ-butyrolactone into 1,4-butanediol was performed using each of the reduced catalysts.

After placing 3.0 g of each of calcined catalysts in a stainless steel reactor having an inner diameter of about 0.25 inch, the calcined catalysts were reduced at about 300° C. for about 12 hours by slowly increasing a temperature of the reactor while flowing a 5% H$_2$/N$_2$ mixed gas through the reactor. γ-butyrolactone was spray-vaporized with hydrogen gas such that the spray-vaporized γ-butyrolactone was supplied to the top of the reactor in a WHSV of about 0.5/h to about 1/h through a 0.0625 inch line. The reaction was performed under conditions including a reaction pressure of about 40 atm to about 60 atm, a reaction temperature of about 150° C. to about 170° C., and a molar ratio of hydrogen gas to γ-butyrolactone from about 50:1 to 100:1 and resulted in the production of 1,4-butanediols.

After about 6 hours from the start of the reaction, produced 1,4-butanediols were cooled at room temperature, and 1 ml of each of the cooled 1,4-butanediols was collected and analyzed by a gas chromatograph (GC). Reaction yields of the respective catalysts were calculated from the analyzed 1,4-butanediols.

2.2 Yield Comparisons According to Reaction Temperatures

The following Table 1 represents yields according to reaction temperatures in hydrogenation reaction of γ-butyrolactone using the respective catalysts.

TABLE 1

| Catalyst | Reaction temperature (° C.) | Pressure (atm) | Hydrogen molar ratio | WHSV (hr$^{-1}$) | Yield (mol %) |
| --- | --- | --- | --- | --- | --- |
| Cu/SiO$_2$—F | 170 | 60 | 100 | 0.5 | 53.2 |
| Cu/SiO$_2$—C | 170 | 60 | 100 | 0.5 | 96.6 |
| Cu/SiO$_2$—C | 150 | 60 | 100 | 0.5 | 50.4 |
| Cu/SiO$_2$—C + K | 150 | 60 | 100 | 0.5 | 99.3 |

As the results in Table 1 indicate, the yield of a reaction using the Cu/SiO$_2$—C catalyst was about 96.6% while that of a reaction using the Cu/SiO$_2$—F catalyst was about 53.2%, under conditions including a reaction temperature of about 170° C., a reaction pressure of about 60 atm, a hydrogen molar ratio of 100, and a WHSV of about 0.5/h. However, in the reaction using the Cu/SiO$_2$—C catalyst, the yield was rapidly dropped to about 50.4% when the reaction temperature was lowered to about 150° C. In comparison, in the reaction using the Cu/SiO$_2$—C+K catalyst, a high yield of about 99% or higher was obtained even at a reaction temperature of about 150° C. As a result of that, it was confirmed that the Cu/SiO$_2$—C+K catalyst maintains very high activity even at a low reaction temperatures.

2.3 Yield Comparisons According to Reaction Pressures

Table 2 represents yields according to reaction pressures in hydrogenation reaction of γ-butyrolactone using the respective catalysts.

TABLE 2

| Catalyst | Reaction temperature (° C.) | Pressure (atm) | Hydrogen molar ratio | WHSV (hr$^{-1}$) | Yield (mol %) |
|---|---|---|---|---|---|
| Cu/SiO$_2$—F | 170 | 60 | 100 | 0.5 | 53.2 |
| Cu/SiO$_2$—C | 170 | 60 | 100 | 0.5 | 96.6 |
| Cu/SiO$_2$—C | 170 | 40 | 100 | 0.5 | 86.7 |
| Cu/SiO$_2$—C + K | 170 | 40 | 100 | 0.5 | 94.7 |

As the results in Table 2 indicate, the yield of a reaction using the Cu/SiO$_2$—C catalyst was about 96.6% while that of a reaction using the Cu/SiO$_2$—F catalyst was about 53.2%, under conditions including a reaction temperature of about 170° C., a reaction pressure of about 60 atm, a hydrogen molar ratio of 100, and a WHSV of about 0.5/h. However, in the reaction using the Cu/SiO$_2$-C catalyst, the yield was dropped to about 86.7% under the reaction pressure of about 40 atm. In comparison, in the reaction using the Cu/SiO$_2$—C+K catalyst, a high yield of about 94.7% was obtained. As a result of that, it was confirmed that a catalyst according to an exemplary embodiment has high activity even at a reduced reaction temperature.

2.4 Yield Comparisons According to Hydrogen Molar Ratios and Space Velocities Table 3 represents yields according to hydrogen molar ratios and space velocities in hydrogenation reaction of γ-butyrolactone using the respective catalysts.

TABLE 3

| Catalyst | Reaction temperature (° C.) | Pressure (atm) | Hydrogen molar ratio | WHSV (hr$^{-1}$) | Yield (mol %) |
|---|---|---|---|---|---|
| Cu/SiO$_2$—F | 170 | 60 | 100 | 0.5 | 53.2 |
| Cu/SiO$_2$—C | 170 | 60 | 100 | 0.5 | 96.6 |
| Cu/SiO$_2$—C + K | 170 | 60 | 75 | 1 | 99.3 |
| Cu/SiO$_2$—C + K | 150 | 60 | 75 | 1 | 99.4 |

As the results in Table 3 indicate, the yield of a reaction using the Cu/SiO$_2$—C catalyst was about 96.6% while that of a reaction using the Cu/SiO$_2$—F catalyst was about 53.2%, under conditions including a reaction temperature of about 170° C., a reaction pressure of about 60 atm, a hydrogen molar ratio of 100, and a WHSV of about 0.5/h. In comparison, in the reaction using the Cu/SiO$_2$—C+K catalyst, a high yield of about 99.3% was obtained although the hydrogen molar ratio was lowered as much as about 25% and the WHSV was increased twice, and a very high yield of about 99.4% was obtained although the reaction temperature was lowered to about 150° C.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for preparing a hydrogenation catalyst, the method comprising:

mixing a copper salt with colloidal silica to form a precipitate;

washing the precipitate to remove an anion of the copper salt from the precipitate; and impregnating the precipitate with an alkali metal to provide a hydrogenation catalyst.

2. The method of claim 1, wherein the copper salt comprises $Cu(NO_3)_2$, $CUCl_2$, $Cu(CH_3COO)_2$, $CuSO_4$, or a combination thereof.

3. The method of claim 1, wherein the precipitate is formed at a pH value of about 8.5 to about 11.

4. The method of claim 1, wherein the copper salt and colloidal silica are mixed in amounts that provide a weight ratio of Cu to $SiO_2$ of about 5:1 to about 3:1.

5. The method of claim 1, wherein the alkali metal is lithium, sodium, potassium, rubidium, cesium, or a combination thereof.

6. The method of claim 1, wherein the precipitate is impregnated with the alkali metal in an amount equal to about $1/20^{th}$ to about $1/4^{th}$ of the weight of $SiO_2$ of the colloidal silica to be mixed with the copper salt.

7. The method of claim 1, further comprising drying the precipitate before the impregnating of the precipitate with the alkali metal.

8. The method of claim 1, further comprising drying and calcining the precipitate after impregnating the precipitate with the alkali metal.

9. A method for preparing a diol from a lactone, the method comprising reacting a lactone and hydrogen in the presence of the hydrogenation catalyst prepared by the method of claim 1 to form a diol.

10. The method of claim 9, wherein the lactone is y-butyrolactone (GBL), β-propiolactone, δ-valerolactone, ε-caprolactone, α-angelica lactone, β-angelica lactone, γ-valerolactone (GVL), or a combination thereof.

11. The method of claim 9, wherein the reaction is performed at a temperature of about 140° C. to about 250° C.

12. The method of claim 9, wherein the reaction is performed at a pressure of about 35 atm to about 65 atm.

13. The method of claim 9, wherein the reaction is performed at a weight hourly space velocity (WHSV) of about 0.3/hr to about 1.5/hr.

14. The method of claim 9, wherein the reaction is performed with a molar ratio of hydrogen to lactone of about 30:1 to about 100:1.

* * * * *